_US005989409A_

United States Patent [19]
Kurnik et al.

[11] Patent Number: 5,989,409
[45] Date of Patent: Nov. 23, 1999

[54] METHOD FOR GLUCOSE SENSING

[75] Inventors: Ronald T. Kurnik, Foster City; Janet Tamada, Belmont; Michael Tierney, San Jose, all of Calif.

[73] Assignee: Cygnus, Inc., Redwood City, Calif.

[21] Appl. No.: 08/526,732

[22] Filed: Sep. 11, 1995

[51] Int. Cl.⁶ .............................. A61N 1/30; A61B 5/00; G01N 27/26

[52] U.S. Cl. ........................... 205/792; 604/20; 128/637; 204/403; 204/412

[58] Field of Search ............................ 604/20, 289, 290; 204/412, 403, 231; 128/637; 205/792

[56] References Cited

U.S. PATENT DOCUMENTS

| | | | |
|---|---|---|---|
| 4,241,150 | 12/1980 | Carr et al. | 429/51 |
| 4,288,507 | 9/1981 | Carr et al. | 429/209 |
| 4,324,257 | 4/1982 | Albarda et al. | 204/403 |
| 4,416,274 | 11/1983 | Jacobsen et al. | 604/20 |
| 4,457,748 | 7/1984 | Lattin et al. | 604/20 |
| 4,477,971 | 10/1984 | Jacobsen et al. | 29/877 |
| 4,546,312 | 10/1985 | Brun et al. | 324/61 P |
| 4,633,879 | 1/1987 | Ong | 128/641 |
| 4,702,732 | 10/1987 | Powers et al. | 604/20 |
| 4,722,726 | 2/1988 | Sanderson et al. | 604/20 |
| 4,722,761 | 2/1988 | Cartmell et al. | 156/242 |
| 4,731,049 | 3/1988 | Parsi | 604/20 |
| 4,752,285 | 6/1988 | Petelenz et al. | 604/20 |
| 4,781,798 | 11/1988 | Gough | 204/412 |
| 4,871,440 | 10/1989 | Nagata et al. | 204/403 |
| 4,968,297 | 11/1990 | Jacobsen et al. | 604/20 |
| 5,036,861 | 8/1991 | Sembrowich et al. | 128/763 |
| 5,135,480 | 8/1992 | Bannon et al. | 604/20 |
| 5,140,985 | 8/1992 | Schroeder et al. | 128/632 |
| 5,250,022 | 10/1993 | Chien et al. | 604/20 |
| 5,279,543 | 1/1994 | Glikfeld et al. | 604/20 |
| 5,362,307 | 11/1994 | Guy et al. | 604/20 |
| 5,423,739 | 6/1995 | Phipps et al. | 604/20 |
| 5,443,442 | 8/1995 | Phipps et al. | 604/20 |

FOREIGN PATENT DOCUMENTS

| | | |
|---|---|---|
| 0 304 304 | 2/1989 | European Pat. Off. . |
| 3737059 | 5/1989 | Germany . |
| 1827524 | 7/1993 | U.S.S.R. . |
| 9012314 | 10/1990 | WIPO . |
| WO 93/24828 | 12/1993 | WIPO . |

OTHER PUBLICATIONS

Derwent abstract of WO 9012314 (Nauer et al.), Oct. 18, 1990.

Flanagan et al., J. Phys. Chem., "Digital Simulation of Edge Effects at Planar Disk Electrodes", (1973) 77:1051–5.

Cassidy et al., Can. J. Chem., "Stimulation of edge effects in electroanalytical experiments by orthogonal collacation. Part 4. Application to voltammetric experiments", (1984) 62:716–20.

Glikfeld et al., Pharm Res (US), "Noninvasive Sampling of Biological Fluids by Iontophoresis", Nov. 1989, 6 (11) pp. 988–990.

Meyerhoff et al., Diabetologia (Germany), "On Line Continuous Montioring of Subcutaneous Tiissue Glucose in Men by Combining Portable Glucosensor with Microdialysis", Nov. 1992, 35 (11) pp. 1087–1092.

*Primary Examiner*—Kathryn L. Gorgos
*Assistant Examiner*—Alexander Noguerola
*Attorney, Agent, or Firm*—Gary R. Fabian; Angela P. Horne; Barbara G. McClung

[57] ABSTRACT

A method for measuring the concentration of glucose diffused from a source to a working electrode which assembly includes a scavenging electrode is disclosed. The electrode of the invention is comprised of 1) a working electrode; 2) a scavenging electrode; 3) an electroosmotic electrode; and 4) a electrically insulating gap defined by adjacent edges of 1) and 2) and electrically isolating 1) and 2). The scavenging electrode substantially reduces or eliminates "edge-effects" or error in signal transported to the working electrode via a path which includes a radial vector component, i.e., eliminates chemical signal other than that which moves to the catalytic surface of the working electrode via a path which is substantially perpendicular to catalytic surface of the working electrode.

15 Claims, 5 Drawing Sheets

METHOD FOR GLUCOSE SENSING

FIELD OF THE INVENTION

The invention relates generally to the field of electrodes for electrochemical measurements, specifically electrodes used in the biomedical fields to measure concentrations of biomedically significant compounds.

BACKGROUND OF THE INVENTION

An electrode is the component in an electrochemical cell in contact with the electrolyte through which current can flow by electronic movement. Electrodes, which are essential components of both galvanic (current producing) and electrolytic (current using) cells, can be composed of a number of electrically conductive materials, e.g., lead, zinc, aluminum, copper, iron, nickel, mercury, graphite, gold, or platinum. Examples of electrodes are found in electric cells, where they are dipped in the electrolyte; in medical devices, where the electrode is used to detect electrical impulses emitted by the heart or the brain; and in semiconductor devices, where they perform one or more of the functions of emitting, collecting, or controlling the movements of electrons and ions.

The electrolyte can be any substance that provides ionic conductivity, and through which electrochemically active species can diffuse. Electrolytes can be solid, liquid, or semi-solid (e.g., in the form of a gel). Common electrolytes include sulfuric acid and sodium chloride, which ionize in solution. Electrolytes used in the medical field must have a pH which is sufficiently close to that of the tissue in contact with the electrode (e.g., skin) so as not to cause harm to the tissue over time.

Electrochemically active species that are present in the electrolyte can undergo electrochemical reactions (oxidation or reduction) at the surface of the electrode. The rate at which the electrochemical reactions take place is related to the reactivity of the species, the electrode material, the electrical potential applied to the electrode, and the efficiency at which the electrochemically active species is transported to the electrode surface.

In unstirred electrolytes, such as quiescent liquid solutions and gel electrolytes, diffusion is the main process of transport of electrochemically active species to the electrode surface. The exact nature of the diffusion process is determined by the geometry of the electrode (e.g., planar disk, cylindrical, or spherical), and the geometry of the electrolyte (e.g., semi-infinite large volume, thin disk of gel, etc.). For example, diffusion of electrochemically active species to a spherical electrode in a semi-infinite volume of electrolyte differs from diffusion of electrochemically active species to a planar disk electrode. A constant and predictable pattern of diffusion (i.e., a diffusion pattern that can be predicted by a simple equation) is critical in determining a correlation between the electrochemical current collected, and the concentration of the electrochemically active species in the electrolyte.

However, diffusion of electrochemically active species toward an electrode can not be predicted by a simple equation for every situation. For example, where the electrochemically active species diffuses through a disk-shaped electrolyte toward a smaller disk-shaped electrode in contact with the electrolyte, the current observed at the electrode can not be predicted by a simple equation. In this latter situation, the inaccuracy in the diffusion model is caused by the combination of two different diffusion models. First, in the center of the disk electrode the diffusion of the electroactive species towards the electrode is in a substantially perpendicular direction. Secondly, at the edges of the disk electrode the diffusion comes from both perpendicular and radial directions. The combination of these two different diffusion patterns makes the total current collected at the disk electrode difficult to predict. In addition, the relative contributions of the diffusion fluxes from the axial and radial directions may change over time causing further errors in predicted current.

SUMMARY OF THE INVENTION

The invention features an electrode subassembly comprised of: 1) a working electrode; 2) a scavenging electrode; and 3) an electrically insulating gap defined by the adjacent edges of the working and scavenging electrodes, the gap serving to electrically isolate the working electrode from the scavenging electrode, and preventing any electrical signal generated at the scavenging electrode from interfering with the detection of the electrical signal generated at the working electrode. An electrical potential is maintained on the scavenging electrode in an amount sufficient to catalyze any chemical signal that diffuses toward the working electrode with any component of a radial vector from the area surrounding the electrode subassembly, thus preventing any significant amount of radially diffusing chemical signal from contacting the working electrode. As a result, the working electrode only catalyzes chemical signal that diffuses from a direction substantially perpendicular to the face of the working electrode.

In one embodiment, the scavenging electrode is in the shape of a ring (i.e., annular) that is concentric to a disk-shaped working electrode.

In another embodiment, the working electrode is in the shape of a ring (i.e., annular) that is concentric to an annular scavenging electrode seated within the working electrode.

In another embodiment, the electrode subassembly is provided as a single unit with a counter electrode and a reference electrode.

An object: of the invention is to provide an electrode subassembly composed of working and scavenging electrodes for use with an electrode assembly to accurately, consistently, and quickly measure a diffused electrochemical signal, and to achieve an accurate measurement of the electrochemical signal within a matter of seconds to minutes.

An object of the invention is to provide an electrode with ends that can be readily connected and disconnected from a power source and monitoring device, thus allowing for replacement of the electrode assembly, electrode subassembly, and/or an ionically conductive material (e.g., an electrolytic gel) used with the electrode assembly.

An advantage of the invention is that the electrode can be used to measure very low concentrations of an electrochemical signal in an electrolyte (i.e., an ionically conductive material). For example, the electrode can be used in conjunction with a hydrogel system for monitoring glucose levels in a subject. An electroosmotic electrode (e.g., iontophoresis or reverse iontophoresis electrodes) can be used to electrically draw glucose into the hydrogel. Glucose oxidase (GOD) contained in the hydrogel converts the glucose into gluconic acid and hydrogen peroxide. The electrode subassembly catalyzes the hydrogen peroxide into an electrical signal. This system allows for the continuous and accurate measurement of an inflow of a very small amount of glucose in an electrolyte (e.g., glucose concentrations 10, 500, or 1,000 or more times less than the concentration of glucose in blood).

Another advantage is that the electrode assembly and electrode subassembly are easily and economically produced.

A feature of the electrode subassembly of the invention is that it is small, flat, and thin, having a total surface area in the range of about 0.1 cm$^2$ to 10.0 cm$^2$, and a thickness in the range of about 0.25 μm to 250 μm.

These and other objects, advantages and features of the present invention will become apparent to those persons skilled in the art upon reading the details of the composition, components and size of the invention as set forth below reference being made to the accompanying drawings forming a part hereof wherein like numbers refer to like components throughout.

DESCRIPTION OF THE PREFERRED EMBODIMENTS

Figure 1A:
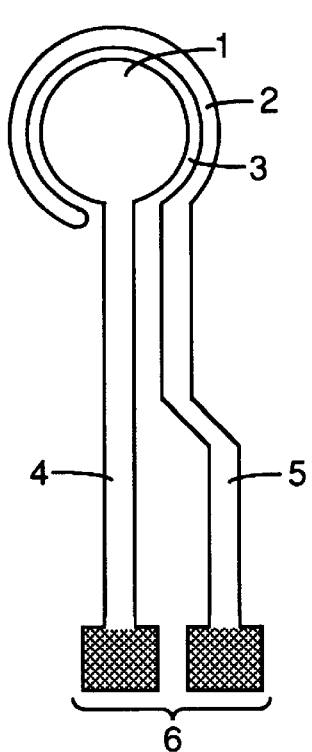
FIGS. 1A and 1B are overhead schematic views of two embodiments of the working and scavenging electrodes (electrode subassemblies) of the invention.

Before the electrode of the present invention is described and disclosed it is to be understood that this invention is not limited to the particular components or composition described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a molecule" includes a plurality of molecules and different types of molecules.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited in connection with.

Definitions

The term "electrode subassembly" means a working electrode and scavenging electrode assembly, where the adjacent edges of the working electrode and the scavenging electrode define an electrically insulating gap. The electrically insulating gap is of a width sufficient to electrically isolate the working electrode from the scavenging electrode. Alternatively or in addition, the gap can contain an electrically insulating material to electrically isolate the working and scavenging electrodes.

The term "electrode assembly" means an assembly comprised of 1) an electrode subassembly, 2) an electroosmotic electrode (e.g., iontophoresis electrode), and 3) reference and counter electrodes. The electrode assembly can additionally include a substrate (e.g., a ceramic or polymeric substrate) to which the electrode assembly and electroosmotic, reference, and counter electrodes are attached.

The term "working electrode" means the electrode that is monitored to determine the amount of electrical signal generated at the electrode subassembly, which is then correlated with the amount of a chemical compound present in the electrolyte. The working electrode comprises a catalytic surface which catalysis the conversion of chemical signal to electrical signal which surface is comprised of a material selected from the group consisting of platinum, palladium, nickel, carbon, noble metals (e.g., gold), and oxides, dioxides and alloys thereof.

The term "scavenging electrode" means the electrode that catalyzes the conversion of chemical signal normally associated with edge effects at the working electrode into products that are not detected by the working electrode, i.e., the scavenging electrode "consumes" excess chemical compound that would otherwise accumulate by radial (i.e., non-axial) diffusion toward the working electrode edges, thereby causing edge effects in the electrical current generated at the working electrode. The electrical signal generated by the scavenging electrode is not monitored for the purpose of measuring the amount of chemical signal present in the electrolyte.

The term "electrically insulating gap" means the space defined by the adjacent edges of the working and scavenging electrodes. The electrically insulating gap electrically isolates the working electrode from the scavenging electrode by virtue of the width of the gap itself, and/or by virtue of an electrically insulating material contained within the gap.

The term "catalytic surface" or "catalytic face" are used interchangeably herein to mean the surface of the working or scavenging electrode that: 1) is in contact with the surface of an electrolyte containing material through which the chemical signal flows from a source of chemical signal; 2) is comprised of a catalytic material (e.g., platinum, palladium, or nickel and/or oxides, dioxides and alloys thereof); 3) catalyzes the conversion of the chemical signal into an electrical signal (i.e., an electrical current); and 4) defines the electrode surface area that, when composed of a catalytic material, is sufficient to drive the electrochemical reaction at a rate sufficient to generate a detectable, accurate electrical signal that is correlatable with the amount of chemical signal present in the electrolyte only that electrical signal generated at the catalytic surface of the working electrode is correlated with the amount of chemical signal present in the electrolyte.

The term "chemical signal," "electrochemical signal," or "electrochemical compound" are used interchangeably and mean the chemical compound that is ultimately converted to an electrical signal at the catalytic faces of the electrode subassembly. "Chemical signals" can be: 1) directly converted into an electrical current by chemical reaction at the catalytic face of the electrode assembly; or 2) indirectly converted into an electrical signal by the action of one or more catalysts. For example, the chemical signal glucose is indirectly converted into an electrical signal by reactions driven by two catalysts. A first catalyst glucose oxidase (GOD), which is present in the electrolyte containing material (e.g., a hydrogel patch), converts glucose into gluconic acid and hydrogen peroxide. Hydrogen peroxide is then converted to a measured electrical current upon electrochemical reduction by platinum (the second catalyst) on the catalytic face of the working electrode. Preferably, the chemical signal is a biomedically significant compound (e.g., glucose).

"Ionically conductive material" means a material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage of electrochemically active species, especially the chemical signal of interest, through it.

Electrode (General)

The invention must have some basic characteristics in order to be useful for its intended purpose, which is to detect a chemical signal in a manner such that the amount of signal detected can be related to the amount of signal in a given source, e.g., detect hydrogen peroxide generated by glucose oxidase (GOD) catalysis of glucose. The electrode assembly must: (1) enable an electric current to flow in the presence of an electrolyte; (2) be easy and inexpensive to manufacture; (3) have a size such that the surface area of one face of the electrode assembly is in the range of about 0.1 cm$^2$ to 10.0 cm$^2$, and a thickness of less than 1 mm wherein all components of the electrode assembly are in substantially the same plane; and (4) include an electrode subassembly having a scavenging electrode component which: a) catalyzes substantially all chemical signals which diffuse radially inward from the area surrounding the working electrode; and b) is electrically insulated from the working electrode.

As used herein, "surface area" means the geometric surface area (e.g., the geometric surface area of a circular electrode defined by the formula $\pi r^2$) without accounting for microscopic surface roughness that can contribute to the actual, three-dimensional surface area. The microscopic surface area is important in considering the actual, three-dimensional surface area available to, for example, drive the electrochemical conversion of the chemical signal to an electrical signal.

For reasons that may relate to factors such as the build up of undesired materials in the electrode assembly and/or electrode subassembly, the electrode assembly and/or electrode subassembly must be easily replaceable (e.g., by a patient) in a convenient manner. In general, the electrode assembly and/or electrode subassembly is designed for use in continuous chemical signal sensing over a period ranging from about 1 day to 1 week, preferably about 1 week to 2 weeks, more preferably about 2 weeks to 4 weeks or more. After such time, the electrode is preferably designed so that it is disposable (e.g., can be readily detached from the monitoring device and replaced with a new electrode subassembly and/or electrode assembly). Accordingly, the electrode assembly must have some structural integrity, and provide for the detection of the chemical signal of interest. In that the electrode assembly and sensor housing containing the electrode assembly is preferably small (e.g., hand held, e.g., the size of a watch to be worn on the wrist of a patient), it is necessary that the electrode assembly and electrode subassembly be particularly thin, e.g., in the range of 0.25 μm to 250 μm. In order to accurately measure the amount of a chemical signal (e.g., the amount of hydrogen peroxide generated by GOD catalysis of glucose) and be sufficiently large to be manipulated, the electrode assembly cannot be too thin and cannot be too small.

The overall surface area of the complete electrode assembly (which includes the electrode subassembly) on a single surface should be in the range of about 0.25 cm$^2$ to about 10 cm$^2$, preferably about 0.50 cm$^2$ to 2 cm$^2$. The electrode subassembly surface area should be in the range from about 0.1 cm$^2$ to about 8 cm$^2$. Where the electrode assembly is used in connection with an ionically conductive material (e.g., a hydrogel patch), the surface area of the electrode assembly is less than the surface area of the ionically conductive material. In general, the surface area of the ionically conductive material for use with the electrode assembly and electrode subassembly of the invention range from about 0.5 cm$^2$ to about 10 cm$^2$, preferably about 1 cm$^2$ to about 5 cm$^2$.

The monitoring of a chemical signal diffused through a surface can be accomplished using a single electrode assembly of the invention. In a preferred embodiment, two complete electrode assemblies, each positioned on adjacent, electrically isolated electrolyte surfaces, are used to monitor the chemical signal.

Basic Structure of the Electrode Subassembly

Figure 1B:
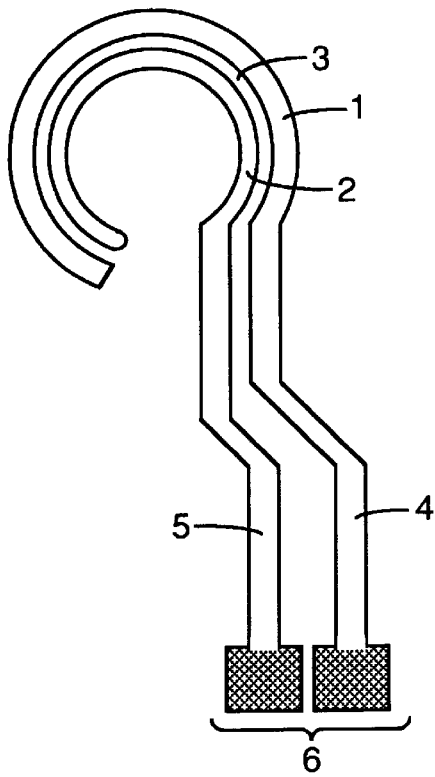

FIGS. 1A and 1B are overhead schematic views of two exemplary embodiments of the electrode subassembly of the invention. The basic structural components of the electrode subassembly are the working electrode 1 and the scavenging electrode 2. These components can be configured in a variety of ways. For example, the scavenging electrode 2 can be in the shape of a closed or nearly completely closed ring (i.e., annular) that is concentric to and surrounds a disk-shaped working electrode 1, as shown in FIG. 1A. Alternatively, the working electrode 1 is annular, and completely or nearly completely surrounds and is concentric to an annular scavenging electrode 2, as shown in FIG. 1B. Reference, counter, and electroosmotic electrodes of the electrode assembly are positioned around the electrode subassembly configuration of FIG. 1A, or seated within and substantially concentric to the electrode subassembly configuration of FIG. 1B.

The working electrode 1 and scavenging electrode 2 in each embodiment are separated by an electrically insulating gap 3 defined by immediately adjacent edges of the working electrode 1 and scavenging electrode 2. In each configuration, the working and scavenging electrodes are in substantially the same plane, and are of substantially the same thickness. The working electrode 1 and the scavenging electrode 2 are each connected by leads 4 and 5 to a power source and monitoring device for respectively generating an electric current through the electrodes, and measuring the electric current generated at the working electrode 1.

The electrode subassembly can also be configured in a variety of ways with respect to the configuration of the electrically insulating gap. The electrically insulating gap 3 can be an empty space between the working and scavenging electrodes, the width of the gap serving to electrically isolate the two electrodes. Alternatively, the electrically insulating gap can contain an electrically insulating material of substantially the same thickness as the working and scavenging electrodes, and separating the working and scavenging electrodes. The electrically insulating material can be configured as a single piece, or can be present as several smaller pieces of material positioned at various points along the working and scavenging electrodes' adjacent edges. The electrically insulating material can contact substantially the entire perimeter of the adjacent electrodes' edges, or contact only portions of one or both of the working and/or scavenging electrode edges. Alternatively, the electrically insulating material can be an area of substrate between the two electrodes on which no electrically conductive material is coated (e.g., the ceramic substrate onto which the electrode assembly is printed can serve as the electrically insulating material).

In general, the width of the electrically insulating gap (and/or the width and location of the electrically insulating material contained in the gap) will vary according to a variety of factors such as the width of the scavenging electrode, the thickness of a ionically conductive material (e.g., hydrogel patch) used with the electrode assembly, the diffusion characteristics of the chemical signal to be detected by the electrode subassembly for a given geometry, the size of the electrode subassembly, and the duration of the sensing period (i.e., monitoring period). For example, where the electrode assembly is used with an electrolytic hydrogel patch having a thickness in the range of about 100 $\mu$m to 700 $\mu$m, the scavenging electrode has a width of greater than 100 $\mu$m, preferably greater than 500 $\mu$m, and the electrically insulating gap has a width in the range of about 50 $\mu$m to 1,000 $\mu$m. In general, as the thickness of the ionically conductive material and the width of the scavenging electrode and electrically insulating gap are directly correlated (e.g., the thicker the gel, the wider the scavenging electrode and electrically insulating gap).

In a preferred embodiment, the ionically conductive material is from about 20 mil to 30 mil thick, the scavenging electrode is about 20 mil wide, and the gap is about 8 mil wide. In general, the width of the scavenging can vary with the thickness of the ionically conductive material (e.g., the hydrogel) such that the width of the scavenging electrode increases as the thickness of the jonically conductive material increases. For example, where the electrode subassembly is used with a hydrogel has a thickness of about 200 $\mu$m, the scavenging electrode is about 500 $\mu$m (e.g., the radius of the outer scavenging electrode perimeter minus the radius of the inner scavenging electrode perimeter).

The Working and Scavenging Electrodes

The working and scavenging electrodes are preferably composed of the same material. Preferably, both the working and scavenging electrodes have the same catalytic material on their catalytic surfaces, preferably Pt, PtO and/or PtO$_2$. The catalytic surface of the working and scavenging electrodes is the face of the electrode in contact with the electrolyte (e.g., a hydrogel patch) and which is responsible for conversion of chemical signal to electrical signal, and thus the face which constitutes the minimal portion of the electrode that must be composed of the catalytic material. The catalytic material of the catalytic surface is the material that promotes conversion of the chemical signal into an electrical signal. Exemplary catalytic materials include carbon as well as platinum, palladium, gold, iridium, or other nobel metal. Where the chemical signal to be detected is hydrogen peroxide (e.g., generated by catalysis of glucose by GOD), the preferred catalytic materials on the catalytic surfaces of the working and scavenging electrodes are platinum, palladium, iridium, or other nobel metal, more preferably platinum or oxides, dioxides or alloys thereof.

The working and scavenging electrodes can be porous or non-porous, preferably non-porous. The working and scavenging electrodes can be made of a single catalytic material (e.g., stamped from a thin sheet of platinum). Alternatively, the working and scavenging electrodes can be plated (e.g., electrolytic or non-electrolytic plating), coated, printed, photolithographically deposited, or otherwise affixed to a substrate using methods well known in the art for application of a thin metal layer on a surface. The substrate can be composed of any insulating material (e.g., a ceramic, plastic (e.g., polyethylene, polypropylene), or polymeric material) to which the electrode assembly can be affixed. Preferably the electrode subassembly, more preferably the complete electrode assembly, is affixed to a plastic or ceramic substrate.

Preferably, the electrode subassembly and electrode assembly are manufactured in a manner that is the most economical without compromising electrode performance (e.g, the ability of tie electrodes to catalyze the chemical signal, and/or conduct an electrical current, or the ability to manipulate the electrodes by hand without breaking or otherwise compromising the operability of the electrodes).

The working and scavenging electrodes can have the catalytic material over all electrode surfaces. Alternatively, only the catalytic faces of the electrode subassembly have the catalytic material. Preferably, the catalytic material is platinum or a platinum-containing material which is present on at least the catalytic surface of the working and scavenging electrodes.

The electrode assembly and/or electrode subassembly can include additional materials that enhance the performance, handleability, and/or durability of the electrode assembly and/or electrode subassembly. For example, the working and scavenging electrodes can be coated with a material that serves to decrease the interference of other species in the electrolyte with the measurement of electric current at the working electrode, and/or decrease the rate of oxidation of the catalytic material on the working and scavenging electrodes' catalytic surfaces.

The relative size (i.e., diameter, surface area, thickness, etc.) of the working and scavenging electrodes can vary according to a variety of factors, including the dimensions of the surface through which the chemical signal is to be detected (e.g., the size of a hydrogel patch through which the chemical signal is drawn), or the size constraints of a monitoring electrode assembly used in connection with the electrode subassembly. The working and scavenging electrodes are normally quite thin, with an average thickness in the range of 0.25 $\mu$m to 250 $\mu$m.

Regardless of the embodiment used, all of the electrode subassemblies of the invention include the three basic components: 1) a working electrode; 2) a scavenging electrode; and 3) an electrically insulating gap defined by the adjacent edges of 1) and 2), which gap electrically isolates 1) and 2). The relative proportions of each of the components (e.g., the width, surface areas, and geometries of the scavenging electrode and the working electrode, and the width of the insulating gap) is such that substantially all chemical signal diffusing toward an edge of the working electrode in a direction having a radial component is electrochemically converted at the scavenging electrode, thus permitting only that chemical signal diffusing in a direction substantially perpendicular to the catalytic face of the working electrode to be electrochemically converted into a measured electrical signal at the working electrode. In addition, the insulating gap is of a width sufficient to electrically isolate the working electrode from the scavenging electrode, but not so wide as to create an region on the ionically conductive material that serves as a source of chemical signal that is not consumed by the scavenging electrode, and thus can radially diffuse toward the working electrode.

The electrode subassembly is normally used in an electrode assembly which includes additional components such as: a) an electroosmotic electrode (e.g., an iontophoresis or reverse iontophoresis electrode); b) a counter electrode; and c) a reference electrode. The electroosmotic electrode can be used to electrically draw electrochemical compounds from a source through material comprising water, enzyme and electrolyte, and to the area of the electrode subassembly. In general, practical and physical limitations of the system require that the electroosmotic electrode and the electrode subassembly be used alternately (i.e., current is present in the electroosmotic electrode or the electric current generated at the electrode subassembly is measured). Alternatively, diffusion of the chemical signal into the ionically conductive material can occur independent of the electroosmotic electrode (e.g., by passive diffusion).

The electrode subassembly can be operated by connecting the electrodes such that the working and scavenging electrodes are connected as two conventional working electrodes, along with appropriate counter and reference electrodes, to a standard bipotentiostat circuit. A bipotentiostat is an electrical circuit used in electrochemical measurements when two independent working electrodes are biased at a common or different potentials versus a reference electrode. The current generated at both electrodes can be measured independently. For the purpose of the present invention, the electrical current measured at the working electrode of the electrode subassembly is the current that is correlated with an amount of chemical signal.

Figure 2:
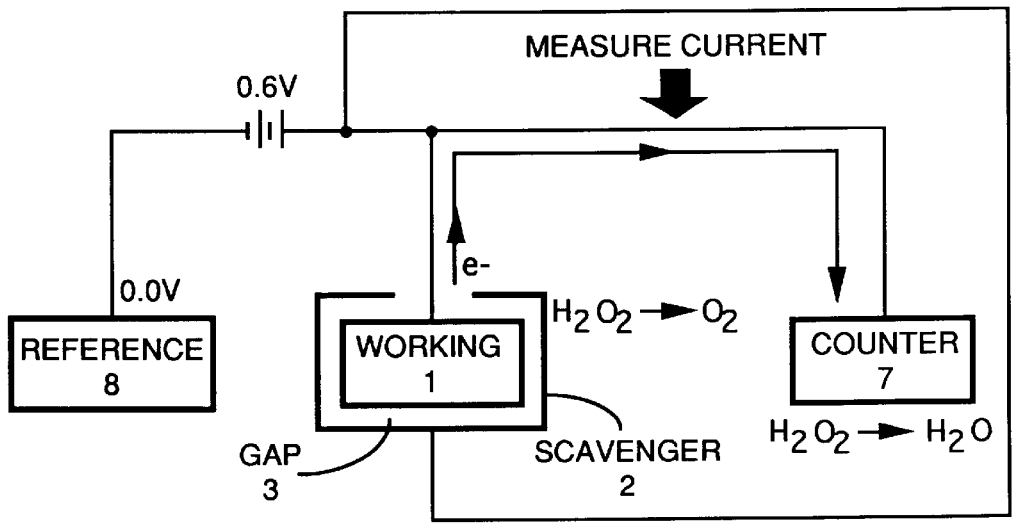
FIG. 2 is a schematic of an operating circuit for the electrode subassembly of the invention.

FIG. 2 illustrates an example of an operating circuit using working 1, scavenger 2, reference 8, and counter 7 with a power source and monitoring device. The power source is used to provide voltage to the reference 8, working 1, and scavenging 2 electrodes to drive the conversion of chemical signal to electrical signal at the catalytic faces of the working 1 and scavenging 2 electrodes. The power source also maintains a fixed potential at the working electrode 1 (where, for example, hydrogen peroxide is converted to molecular oxygen, hydrogen ions, and electrons), which is compared with the potential of the reference electrode 8 during monitoring. The operating circuit also maintains an electrical potential on the scavenging electrode 2 for catalysis of chemical signal which diffuses radially inward toward the working electrode 1, and on the working electrode 1 for catalysis of chemical signal that diffuses axially toward the working electrode 1. The working electrode 1 is electrically connected to a counter electrode 7. The counter electrode 7 consumes electrons generated at the working electrode 1 and scavenging electrode 2 (e.g., by conversion of hydrogen peroxide to water). In this example, the scavenger electrode 2 surrounds the working electrode 1, and is electrically connected to the power source at a position outside of the electrical connection between the working 1 and counter 7 electrodes. The electrically insulating gap 3 between the working 1 and scavenging 2 electrodes serves to electrically isolate these two electrodes. The current generated at the working electrode 1 is measured at a position between the working 1 and counter 7 electrode, thus avoiding interference with any current generated at the scavenging electrode 2.

Based on the description above and in the figures, it will be recognized that the electrode subassembly and electrode assembly of the invention can be configured in a variety of different forms, and from a variety of different materials. However, the electrodes will have certain defined mechanical, electrical, chemical and diffusion characteristics.

Mechanically the electrode assembly and electrode subassembly will have sufficient structural integrity such that it can be readily handled by human fingers without significant handling difficulties or significantly compromising the performance of the electrode. Further, where the electrode subassembly is used in conjunction with an ionically conductive material (e.g., a hydrogel patch), it may be desirable to remove the material from the electrode. Thus, it may be desirable to design the electrode so thaw the patch can be removed from the electrode assembly and electrode subassembly without significantly degrading the surface of the electrodes, or adhering to the electrodes in a manner that makes it difficult to completely remove all patch material from the face of the electrodes. The electrode subassembly and/or electrode assembly can be provided as a unit separate from the any other component of a monitoring device (e.g., a glucose monitoring device). Alternatively, the tonically conductive material and the electrode subassembly and/or electrode assembly can be provided as a single unit.

Preferably, the electrode will optimally operate at a pH which is relatively close to that of the solid or electrolyte in which the electrode subassembly is in contact (e.g, human skin (about 7), hydrogel patch) and at least within a range of from about pH 4 to pH 9. In general, the working electrode and the scavenging electrode operate at a current level in the range of 1 nanoamp to 1 milliamp.

Utility

The present invention is useful in connection with the detection of biologically significant molecules such as glucose which are moved through human skin using a technique known as electroosmosis. The basic concept of moving a molecule such as a glucose through human skin is disclosed within U.S. Pat. No. 5,362,307, issued Nov. 8, 1994 and U.S. Pat. No. 5,279,543, issued Jan. 18, 1994 which patents are incorporated herein by reference for disclosing the basic concept of moving molecules such as glucose through human skin by means of electroosmosis. The concept of converting the very small amounts of molecules such as glucose which can be extracted through the skin in order to create a current by use of glucose oxidase is disclosed within earlier filed application Ser. No. 08/265,084, filed Jun. 24, 1994 and application Ser. No. 08/373,931, filed Jan. 10, 1995; and hydrogel patches suitable for use with the present invention are disclosed within earlier filed application Ser. No. 08/501,664, filed Jul. 12, 1995, each of which applications are incorporated herein by reference in their entirety and which applications disclose inventions which were invented under an obligation to assign rights to the same entity as which the rights in the present invention were invented under an obligation to assign to.

Figure 3A:
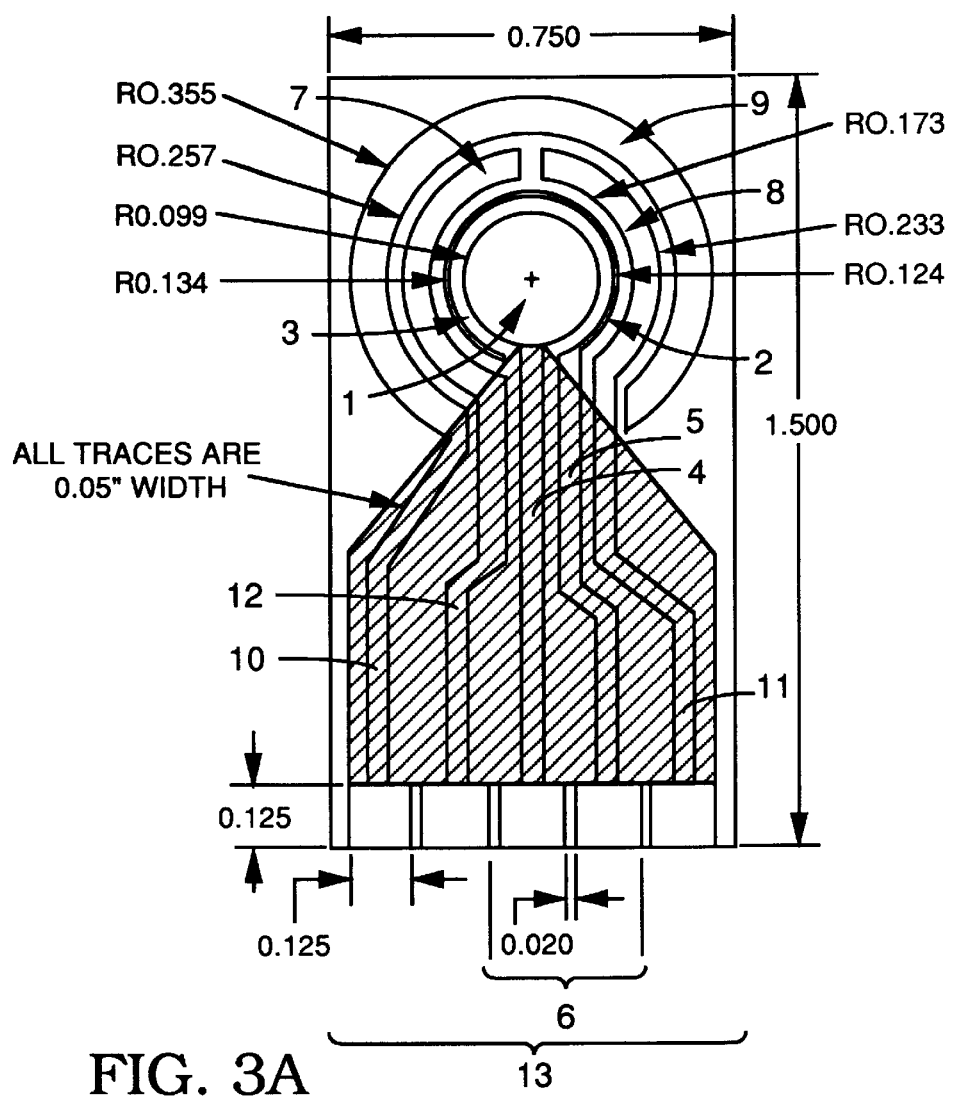
FIG. 3A is an overhead schematic view of the electrode subassembly as it can be configured as a component of an electrode assembly.
Figure 3B:
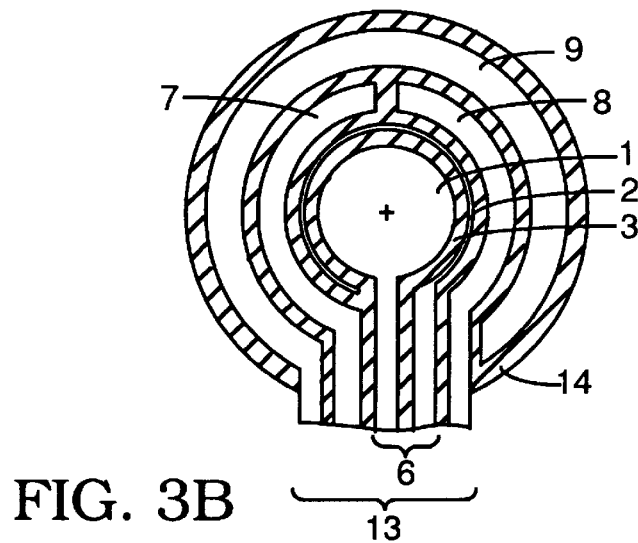
FIGS. 3B and 3C are overhead and cross-sectional schematic views of the sensing and scavenging electrodes as they may be used in conjunction with reference, counter, and electroosmotic electrodes and a hydrogel patch.
Figure 3C:
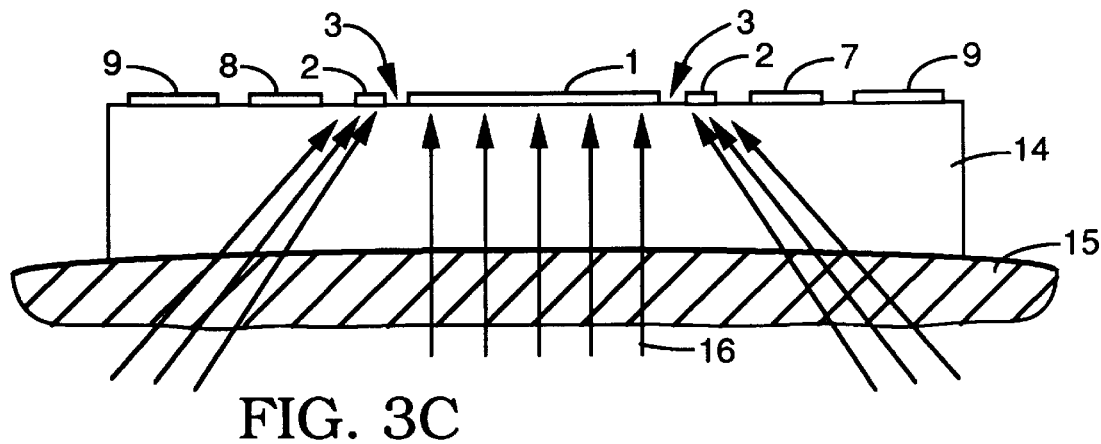
Figure 4:
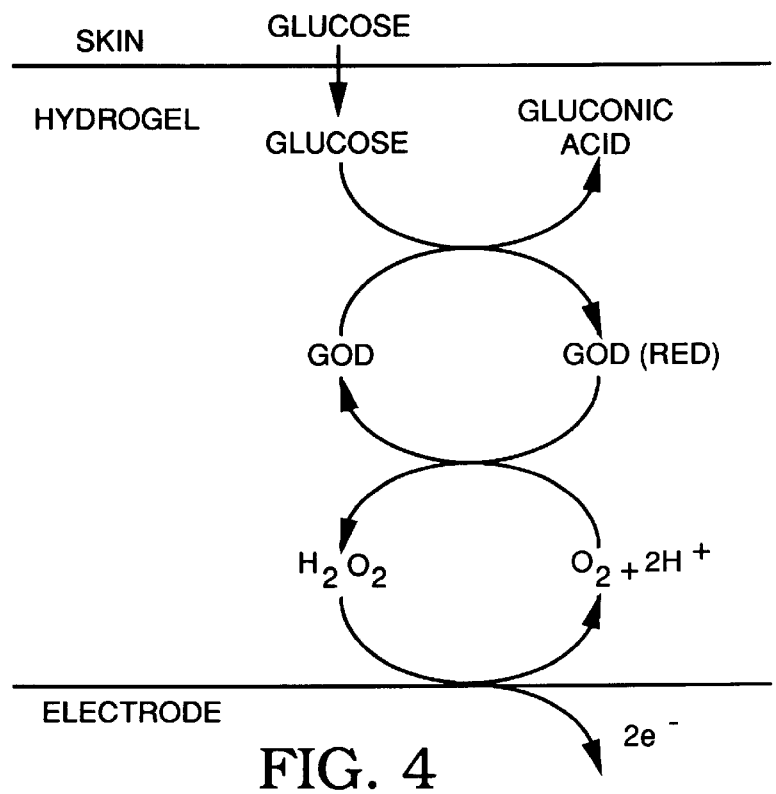
FIG. 4 is a schematic representation of the reaction which glucose oxidase (GOD) catalyzes to produce gluconic acid and hydrogen peroxide; hydrogen peroxide is then electrochemically reduced at the working electrode, thereby producing 2 electrons in the sensing circuit.

The electrode subassembly of the invention can be used as part of an electrode assembly (e.g., with reference, counter, and electroosmotic electrodes) for measurement of a biomedically important compound (e.g., glucose). For example, as shown in FIG. 3A, the electrode subassembly 6 can be placed within a electroosmotic electrode 9, a reference electrode 8 and a counter electrode 7. The electroosmotic 9, reference 8. and counter 7 electrodes are connected by leads 10, 11, and 12 respectively to a power source and monitoring device. A hydrogel patch 14 is placed in contact with the electrode assembly as shown in FIG. 3B, and the entire assembly placed onto an area of mammalian (e.g., human) skin 15 as shown in FIG. 3C. An electrical current is sent through the electroosmotic electrode, thereby drawing molecules 16, including glucose, through the patient's skin and into the hydrogel patch. Glucose oxidase (GOD), contained in the hydrogel patch, catalyzes the conversion of glucose into gluconic acid and hydrogen peroxide as described above and shown in FIG. 4. The hydrogen peroxide is then catalyzed at the electrode subassembly 6 to 2 electrons, molecular oxygen, and 2 hydrogen ions, and the electric current generated at the working electrode 1 measured relative to the reference electrode 8 as exemplified in FIG. 2. The electrical current generated at the working electrode 1 is correlated to the amount of glucose in the hydrogel patch, and extrapolated to the concentration of glucose in the subject's bloodstream.

The composition, size and thickness of the electrode assembly can be varied and such variance can affect the time over which the electrode assembly can be used. For example, the hydrogel patches and the electrodes of the present invention used with the electrode assembly are generally designed so as to provide utility over a period of about 24 hours. After that time some deterioration in characteristics, sensitivity, and accuracy of the measurements from the electrode can be expected (e.g., due to accumulation of material on the face of the electrode subassembly), and the electrode subassembly and hydrogel patch should be replaced. The invention contemplates electrode assemblies which are used over a shorter period of time e.g., 8 to 12 hours or a longer period of time e.g., 1 to 30 days.

In its broader sense, an electrode of the invention can be used to carry out a method which comprises extracting any biomedically significant substance through the skin of a mammalian subject: (e.g., a human patient) and reacting that substance with another substance or substances to form a product which is detectable electrochemically by the production of a signal, which signal is generated proportionally based on the amount of a biologically important or biomedically significant substance drawn into the patch. As indicated in the above-cited patents the ability to withdraw biochemically significant substances such as glucose through skin has been established (see U.S. Pat. Nos. 5,362,307 and 5,279,543). However, the amount of compound withdrawn is often so small that it is not possible to make meaningful use of such methodology in that the withdrawn material cannot be precisely measured and related to any standard. The present invention provides an electrode that is capable of detecting the electrochemical signal at very low levels in a manner that allows for direct, accurate correlation between the amount of signal generated and the amount of the molecule in the human subject.

The invention is remarkable in that it allows for the noninvasive detection and quick, accurate measurement of amounts of a biomedically relevant compound, e.g., glucose, at levels that are 1, 2, or even 3 orders of magnitude less than the concentration of that compound in blood. For example, glucose might be present in blood in a concentration of about 5 millimolar. However, the concentration of glucose in a hydrogel patch which is used to withdraw glucose through skin as described in the system above is on the order of 2 micromolar to 100 micromolar. Micromolar amounts are 3 orders of magnitude less than millimolar amounts. The ability to accurately and quickly detect glucose in such small concentrations is attained by constructing the electrode assembly and electrode subassembly with the components described herein and the configurations described herein.

EXAMPLES

The following examples are put forth so as to provide those of ordinary skill in the art with a complete disclosure and description of how to mask and use the electrode assemblies and subassemblies of the present invention and are not intended to limit the scope of what the inventors regard as their invention. The data presented in these examples are computer-simulated (i.e., the data is generated from a computer model of the mask and electrode assembly described herein). The computer model of the invention uses the following parameters:

glucose diffusivity: $1.3 \times 10^{-6}$ cm$^2$/sec;
peroxide diffusivity: $1.2 \times 10^{-5}$ cm$^2$/sec;
enzyme rate constant: 735 sec$^{-1}$;
$K_M$ for glucose: $1.1 \times 10^5$ nmol/ml;
$K_M$ for glucose: 200 nmol/ml;
initial oxygen concentration: 240 nmol/ml;
enzyme loading in gel: 100 U/ml; and
glucose flux: 5 nmol/cm$^2$ hr.

Efforts have been made to ensure accuracy with respect to numbers used, (e.g., amounts, particular components, etc.) but some deviations should be accounted for. Unless indicated otherwise, parts are parts by weight, surface area is geometric surface area, temperature is in degrees centigrade, and pressure is at or near atmospheric pressure.

Example 1
(Platinum Electrode—No Scavenger Electrode)

The peroxide flux at a circular (0.4 cm radius), platinum electrode (i.e., without a scavenging electrode) when used in conjunction with an electroosmotic electrode in a glucose monitoring system was determined. For the purposes of this model, the electrode assembly is positioned on top of a hydrogel patch (0.9 cm radius), which contains the enzyme glucose oxidase (GOD). The face of the hydrogel patch is positioned opposite the face in contact with the electrode assembly on a source of chemical signal such as on the arm of a human subject. The leads of the electrode assembly are connected to a glucose monitoring system, which contains a power source and a monitoring means for detecting the electric current generated at the electrode assembly.

Current is supplied to both the reference and platinum electrodes as well as to the electroosmotic electrode. In general, practical limitations of the system require that the electroosmotic electrode and the electrode subassembly be used alternately; however, alternate or simultaneous supply of current to the electroosmotic and working electrodes does not affect the calculation of the peroxide flux at the working electrode catalytic face. The current from the electroosmotic electrode increases the permeability of the subject's skin, thereby drawing glucose molecules from a source, e.g. a subject's bloodstream, and into the hydrogel patch where GOD catalyzes conversion of glucose into hydrogen peroxide and gluconic acid. The platinum-coated catalytic surface of the electrode subassembly converts the hydrogen peroxide into an electrical signal. The resulting electrical current is measured using the monitoring device.

Figure 5:
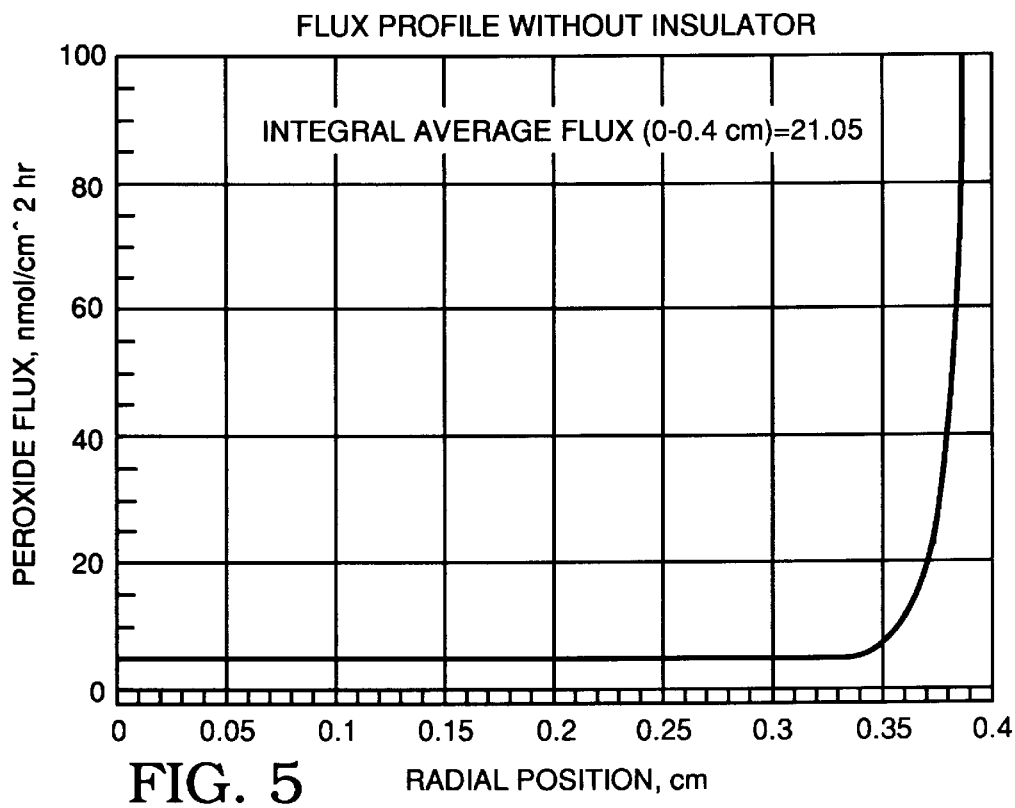
FIG. 5 is a graph showing the calculated position dependence of the peroxide flux on a circular platinum electrode without a scavenging electrode.

After 1 hour total sensing time, the electric current is measured at various positions from the center of the electrode (0 cm) to the electrode edge (0.4 cm). The position dependence of the hydrogen peroxide flux is calculated in this computer simulation and shown in FIG. 5. The results were calculated based on an input glucose flux of 5 nmol/cm$^2$ into a 200 micron width gel with an enzyme loading of 10 U/ml, and with both the biosensor and iontophoretic electrode turned on. As shown in this graph, the measured peroxide flux from the center of the electrode to about a radius of 0.35 cm has the same steady flux as the input glucose flux. At the periphery of the sensor, however, the peroxide flux increases significantly, due to the radial diffusion of peroxide molecules (the edge effect). The calculated current measured from the sensor electrode is proportional to the integral average peroxide flux (calculated by integrating the flux times radius and dividing by the surface area). This integral average flux for the above parameters using an electrode without a scavenging electrode is 21.05 nmol/cm$^2$ hr, which is significantly greater than the input glucose flux of 5 nmol/cm$^2$, due to the edge effect. Thus, these calculations show that use of an electrode without a scavenger electrode results in significant error when attempting to obtain quick, accurate, continuous measurement of glucose levels in a mammalian subject.

Example 2

With Scavenger Electrode

The computer simulation in Example 1 was repeated with an electrode subassembly of the invention (i.e., with a scavenger electrode). The electrode subassembly in this example is composed of a circular, disc-shaped platinum working electrode, an annular platinum scavenging electrode surrounding and concentric to the working electrode, and an electrically insulating gap defined by the adjacent edges of the working and scavenging electrode as shown in FIG. 1A. The electrode subassembly has an insulating gap of 200 microns, and the scavenging electrode has an annular width (difference between the outer and inner radius) of 500 microns.

Figure 6:
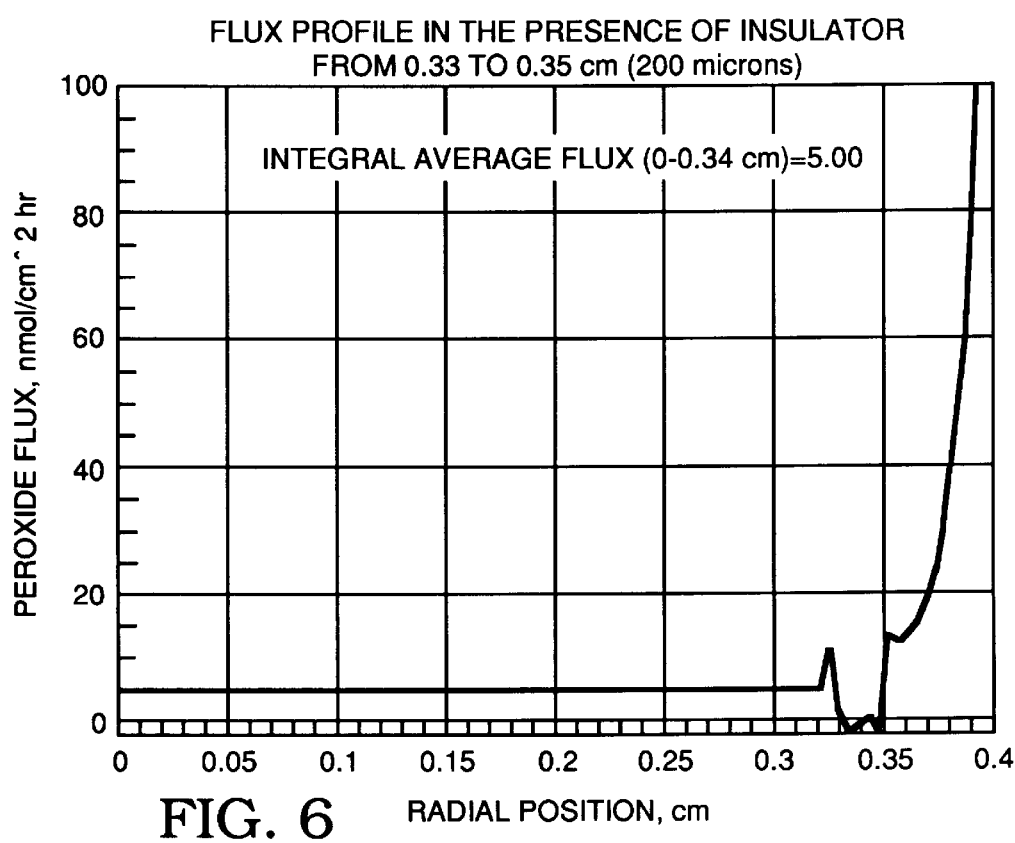
FIG. 6 is a graph showing the calculated position dependence of the peroxide flux at the surface of a working electrode in an electrode subassembly of the invention (i.e., with scavenging electrode and insulating gap).

After 1 hr of sensing, the calculated hydrogen peroxide flux as a function of radial position from the center of the sensor electrode to the periphery of the electrode is shown in FIG. 6. As shown in this graph, the measured peroxide flux from the center of the electrode to a radius of about 0.32 cm has the same steady flux as the input glucose flux. There is a very small increase of the flux near the inner perimeter of the insulating gap, after which the flux drops to zero. At the outer perimeter of the insulating gap the peroxide flux rises rapidly to the edge of the sensor electrode (due to the radial diffusion of the peroxide molecules, which causes the edge effect).

The calculated measured current from the sensor electrode with the scavenger electrode in place is thus proportional to the integral average peroxide flux (calculated by integrating the flux times radius and dividing by the surface area) from the center of the electrode to the middle of the insulating gap. The calculated integral average flux for this example is 5.0 nmol/cm$_2$ hr, which is the same as the glucose flux of 5 nmol/cm$_2$ hr. These calculations show that when the scavenger electrode is in place, there is no or minimal error in determining quick, accurate, continuous measurement of glucose levels in a mammalian subject.

Example 3

With Scavenger Electrode and Alternating on/off of the Iontophoresis/Sensing Electrode The computer simulation of Example 1 was repeated with an electrode subassembly of the invention, except that the current was alternately supplied to the iontophoresis electrode and electrode subassembly. The electrode subassembly for this example is composed of a circular, disc-shaped platinum working electrode, an annular platinum scavenging electrode surrounding and concentric to the working electrode, and an electrically insulating gap defined by the adjacent edges of the working and scavenging electrodes, as shown in FIG. 1A. The insulating gap is 200 microns wider, and the annular width (difference between the outer and inner radius) of 500 microns. In this example one cycle of sensing includes 15 min of iontophoresis, followed by 5 min of measuring the electrical current at the working electrode (i.e., biosensor on). The iontophoresis electrode and the biosensor are alternatively (i.e., not simultaneously) activated.

Figure 7:
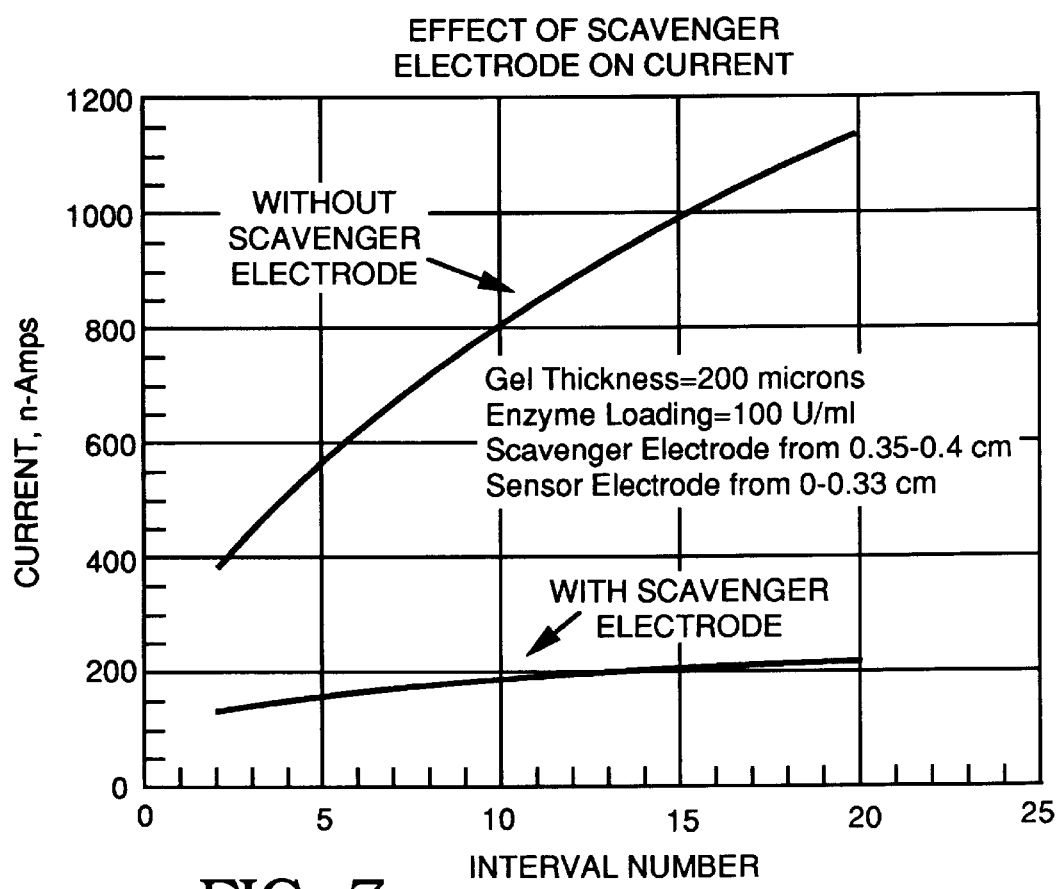
FIG. 7 is a graph showing the calculated measured current at the surface of a platinum electrode (either with a scavenging electrode (i.e., the electrode subassembly of the invention) or without a scavenging electrode) as a function of interval number.

Over 10 cycle period of sensing, the integral average hydrogen peroxide flux as a function of interval number was calculated in the above computer model. This calculation is shown in FIG. 7 for both an electrode assembly of the invention (i.e., with scavenging electrode) and an electrode without the scavenging electrode. It is apparent from this figure that use of the scavenging electrode substantially improves the operating of the biosensor unit by reducing the edge effect, resulting in an integral average flux that is directly correlated to the input glucose flux. Thus, these calculations show that when the scavenger electrode is in place, there is no or minimal error in obtaining quick, accurate, continuous measurement of glucose levels in a mammalian subject.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. A method measuring the concentration of glucose in a mammalian subject, the method comprising the steps of:

contacting a first surface of an ionically conductive material with skin of the mammalian subject;

contacting an electrode assembly to a second surface of the ionically conductive material, the assembly comprising:

(a) a working electrode;
   (b) a scavenging electrode;
   (c) an electrically insulating gap which electrically insulates the scavenging electrode and working electrode; and
   (d) an electroosmotic electrode;

wherein the working electrode and scavenging electrode are in the same plane, the scavenging electrode being positioned such that the scavenging electrode component electrochemically converts chemical compounds that diffuse radially toward the working electrode;

providing current to the electroosmnotic electrode in an amount sufficient to electrically draw glucose across the mammalian subject's skin, through the ionically conductive material and to the working electrode;

providing a voltage to the scavenging electrode in an amount sufficient to drive electrochemical conversion of glucose diffusing in a radial direction toward the working electrode of the electrode assembly;

providing a voltage to the working electrode in an amount sufficient to drive electrochemical conversion of glucose diffusing axially toward the working electrode;

measuring the electrical current generated by the electrochemical conversion at the working electrode; and correlating the measured current to a concentration of glucose in the mammalian subject.

2. The method of claim 1, wherein the working electrode is disc-shaped, and the scavenging electrode is annular and concentric to the working electrode.

3. The method of claim 1, wherein the scavenging electrode and the working electrode are annular, and the working electrode surrounds and is concentric to the scavenging electrode.

4. The method of claim 1, wherein the working electrode and scavenging electrode comprise a platinum catalytic surface.

5. The method of claim 1, wherein the electrically insulating gap has a width in a range of about 50 $\mu$m to 1,000 $\mu$m.

6. The method of claim 1, wherein an electrically insulating material is positioned in the electrically insulating gap.

7. The method of claim 1, wherein the electrode assemnbly is further characterized by a flat configuration and having a thickness in a range of about 0.25 $\mu$m to 250 $\mu$m.

8. The method of claim 1, wherein the elecrtrode assembly is further characterized by a surface area in the range of about 0.1 cm$^2$ to about 8 cm$^2$.

9. The method of claim 1, wherein the scavenging electrode has a width in the range of about 100 $\mu$m to 2,000 $\mu$m.

10. The method of claim 1, which further comprises a counter electrode and a reference electrode, each being positioned in the same plane as the electrode subassembly, the counter electrode being electrically connected to the working electrode, and the reference electrode being positioned such that a constant electrical potential is maintained on the reference electrode relative to the working electrode.

11. The method of claim 1, wherein the electrode subassembly is disposable.

12. The method of claim 1, wherein the working electrode operates at a current level in the range of 1 nanoamp to 1 milliamp and the scavenging electrode operates at a current level in the range of 1 nanoamp to 1 milliamp.

13. The method of claim 1, wherein the electrode assembly further comprises:

d) a counter electrode; and e) a reference electrode;

wherein the working electrode, scavenging electrode, counter electrode, reference electrode, and electroosmotic electrode are in the same plane as, and concentrically aligned with, each other.

14. The method of claim 13, wherein the ionically conductive material comprises:

g) a hydrogel patch, the patch having a surface in contact with a surface of the electrodes (a), (b), (d), (e) and (f).

15. The method of claim 1, wherein the ionically conductive material is a hydrogel comprising water, electrolyte, and glucose oxidase.

* * * * *

UNITED STATES PATENT AND TRADEMARK OFFICE
CERTIFICATE OF CORRECTION

PATENT NO. : 5,989,409
DATED : November 23, 1999
INVENTOR(S) : Ronald T. KURNIK, Janet TAMADA, and Michael TIERNEY It is certified that error appears in the above-identified patent and that said Letters Patent are hereby corrected as shown below:

In column 14, line 60, "electroosmnotic" should be -- electroosmotic --;
In column 15, line 23, "assemnbly" should be -- assembly --; and
In column 15, line 26, "elecrtrode" should be -- electrode --.

Signed and Sealed this

Twenty-second Day of May, 2001

Attest:

NICHOLAS P. GODICI

Attesting Officer

Acting Director of the United States Patent and Trademark Office